United States Patent
Totakura

[11] Patent Number: 5,891,167
[45] Date of Patent: Apr. 6, 1999

[54] COLLAGEN COATED GUT SUTURE

[75] Inventor: Nagabhushanam Totakura, North Haven, Conn.

[73] Assignee: United States Surgical Corporation, Norwalk, Conn.

[21] Appl. No.: 668,024

[22] Filed: Jun. 19, 1996

[51] Int. Cl.[6] .................................................. A61B 17/04
[52] U.S. Cl. .................................... 606/228; 606/231
[58] Field of Search .................................... 606/230, 231, 606/228; 427/2.31; 428/364, 375, 378

[56] References Cited

U.S. PATENT DOCUMENTS

| | | |
|---|---|---|
| 887,130 | 5/1908 | Schmidt . |
| 1,254,031 | 1/1918 | Davis . |
| 1,865,214 | 6/1932 | Saladino et al. . |
| 1,999,641 | 4/1935 | Sharp et al. ............... 128/335.5 |
| 2,039,262 | 4/1936 | Schulte ............................ 18/54 |
| 2,457,804 | 1/1949 | Bower ........................ 128/335.5 |
| 2,475,697 | 7/1949 | Cresswell ........................ 18/54 |
| 2,484,813 | 10/1949 | Bower ........................ 128/335.5 |
| 2,493,943 | 1/1950 | Bower ........................ 128/335.5 |
| 2,524,772 | 10/1950 | Davis et al. ................ 128/335.5 |
| 2,576,576 | 11/1951 | Cresswell et al. ........... 128/335.5 |
| 2,637,321 | 5/1953 | Cresswell .................... 128/335.5 |
| 2,640,752 | 6/1953 | Davis et al. .................... 8/94.11 |
| 3,034,852 | 5/1962 | Nishihara ........................ 18/54 |
| 3,166,073 | 1/1965 | Kronenthal .................. 128/335.5 |
| 3,276,448 | 10/1966 | Kronenthal .................. 128/334 |
| 3,284,557 | 11/1966 | Polansky .................... 264/238 |
| 3,698,853 | 10/1972 | Wilson ........................ 8/94.11 |
| 3,729,007 | 4/1973 | Mirkovitch .................. 128/335.5 |
| 3,808,113 | 4/1974 | Okamura et al. .......... 204/159.12 |
| 4,027,676 | 6/1977 | Mattei ........................ 128/335.5 |
| 4,201,216 | 5/1980 | Mattei ........................ 128/335.5 |
| 4,343,617 | 8/1982 | Baur, Jr. ........................ 8/127.6 |
| 4,433,688 | 2/1984 | Bichon ........................ 128/335.5 |
| 4,506,672 | 3/1985 | Bichon ........................ 128/335.5 |
| 5,089,013 | 2/1992 | Bezwada et al. ............ 606/228 |
| 5,304,205 | 4/1994 | Shinoda et al. ............. 606/230 |
| 5,342,624 | 8/1994 | McNeill et al. .............. 424/451 |
| 5,442,032 | 8/1995 | Arnold et al. ............... 528/354 |

*Primary Examiner*—Gary Jackson

[57] ABSTRACT

A catgut suture includes a dehydrothermal cross-linked collagen coating which is insoluble in tubing solution. The collagen coating is formed by immersing the gut suture in a solution of collagen in acidified water. Optionally, a plasticizer may be included in the coating solution. The suture is then heated in a vacuum to effect cross-linking of the collagen.

3 Claims, 1 Drawing Sheet

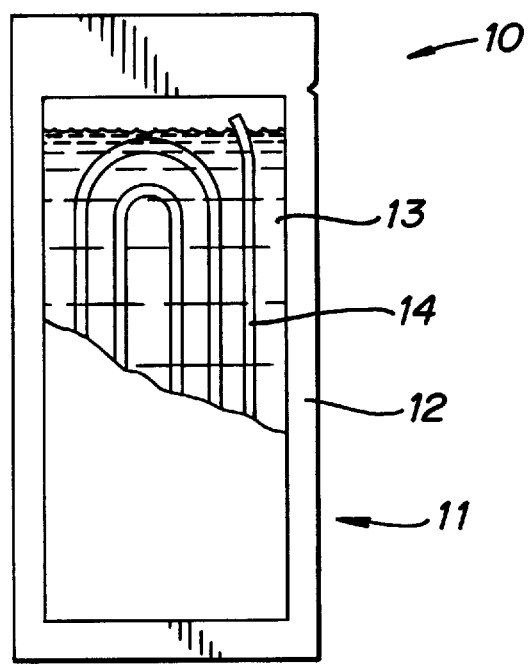
FIG_1
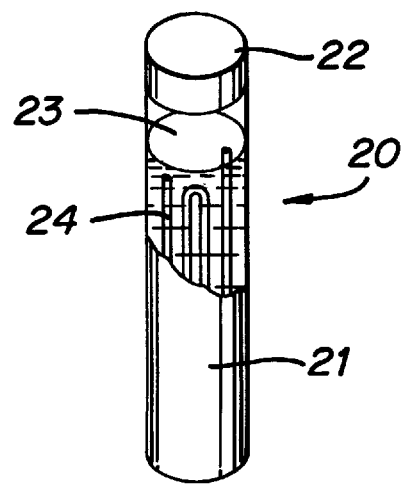
FIG_2

COLLAGEN COATED GUT SUTURE

BACKGROUND

1. Technical Field

The subject matter disclosed and described herein relates to a surgical suture fabricated from gut and coated with collagen, and a method for making same.

2. Background of the Art

Sutures are well known in the art and are often used in surgical procedures for holding cut tissue surfaces in apposition for a period of time sufficient for healing. Non-absorbable sutures, e.g. sutures made from non-bioabsorbable materials such as polyolefins, nylon, cotton, and the like, are generally removed from the tissue after a period of time. Absorbable sutures, e.g. those fabricated from bioabsorbable materials such as polymers of lactide and glycolide, collagen, and the like, are gradually degraded and absorbed by the body, and do not require subsequent removal. Gut sutures are made from the submucosa layer of the intestines of certain mammals (e.g., sheep, beef, etc.) which consist mainly of collagen. In preparing gut sutures and ligatures, animal intestinal tubes are split longitudinally, cleaned and spun or twisted to form strands. Such strands are termed plain catgut and when implanted in animal tissues are normally absorbed within a period of several days by enzymolysis. For many surgical procedures it is necessary for the sutures to retain their strength for a longer period of time to permit a wound or incision to heal properly. Therefore, such sutures are tanned by immersion in a solution of tanning agent such as a chromium salt. Tanning increases the resistance of collagenous material to degradation. Such sutures are termed "chromic catgut".

Surgeons need sutures which are pliable and instantly usable. Unless catgut sutures are stored in a tubing solution, from which they are removed by the surgeon just prior to use, they will dry out and become too hard for use. Such storage solutions are well known in the art and typically include water and alcohol, for example ethyl and/or isopropyl alcohols, and optionally triethanolamine.

SUMMARY

A method for treating a gut suture is provided herein to achieve a gut suture with excellent handling characteristics. The method includes cross-linking a collagen coating by a dehydrothermal process. The collagen cross-linked by the present method remains on the suture even when the suture is immersed in tubing solution and provides improved handling characteristics during a surgical procedure. In particular, the method comprises (a) preparing an acidified aqueous solution of collagen; (b) coating a gut suture with said collagen solution; and (c) heating said coated suture in a vacuum to a temperature above 70° C., and preferably from about 105° C. to about 115° C., for a predetermined period of time. The suture can then be stored in a tubing solution. The tubing solution preferably comprises water isopropanol, and triethanolamine. The aqueous solution of collagen is prepared by dissolving collagen powder in acidified water having a pH of from about 1 to about 6, preferably 2 to 5, and more preferably from about 3 to about 4, and optionally includes a plasticizer such as glycerine. The gut suture prepared by this method can be packaged and stored in tubing solution and has superior handling characteristics during surgical procedures.

BRIEF DESCRIPTION OF THE DRAWINGS

Various embodiments are described herein with reference to the drawings, wherein:

FIGS. 1 and 2 are cut-away views illustrating alternative embodiments of packages for containing the coated catgut suture described herein in tubing fluid.

DETAILED DESCRIPTION OF PREFERRED EMBODIMENTS

The pre-coated catgut sutures used in the method described below may be provided by conventional techniques. By way of illustration, beef serosa ribbons are desalinated and assembled. They are then soaked in wet phase treatment in baths of sodium carbonate, hydrogen peroxide, and water. Plain catguts are then soaked in sodium hydrosulfite and then soft water, whereas chromic catguts are then soaked in pyrogallic acid, sodium bichromate to which sodium bisulfite is later added, and optionally gelatin. After the wet phase treatments the wet catguts are then twisted. This operation blends the serosa lengths before the drying operation which creates chemical liaisons between the collagen molecules. After twisting, the catguts are dried and cut to final length. The catguts are then machine polished. Chromic catguts are further soaked in an aqueous solution of ethanol and glycerine.

The above described process provides catgut sutures which may then be coated in accordance with the method described below. The coating method described herein advantageously provides a collagen coating which surprisingly does not come off the suture even when the suture is stored in tubing solution. Thus, an important distinguishing feature of this method is that the collagen coating remains on the suture when the surgeon removes the suture from the tubing solution and provides improved knot run down and reduced fraying characteristics on an immediately usable suture.

The method described herein comprises three basic steps which will be discussed in greater detail below: (1) soaking the suture in coating agent solution, (2) subjecting the coated suture to a dehydrothermal cross-linking process, and (3) storing the suture in tubing solution.

The coating solution comprises an aqueous solution of collagen in acidified pyrogen free water. The solution can be prepared by dissolving soluble collagen powder in the acidified water and filtering the solution, if necessary. The water preferably has a pH of from about 1 to about 6, more preferably from about 2 to about 5, and most preferably from about 3 to about 4. The water can be acidified by the admixture of inorganic or organic acids such as hydrochloric acid, acetic acid, and the like, in an amount sufficient to lower the pH to the appropriate level. The solution preferably ranges in concentration up to about 2% collagen, more preferably from about 0.01% to about 0.5% collagen, and most preferably from about 0.1% to about 0.2% collagen. Percentages given herein are by weight unless otherwise indicated. Optionally a plasticizer, such as triethylcitrate or glycerine or other polyhydric alcohol, can be included in the coating solution and preferably ranges from between 0.001% to about 0.020% of the coating solution composition, more preferably from about 0.005% to about 0.010% of the coating solution. The ratio of collagen to plasticizer preferably ranges from about 5 to 30, and more preferably from about 10 to 20. The coating solution can be stored in a freezer if necessary. The collagen coating provides beneficial surface properties to the catgut suture by improving surface smoothness and reducing fraying. The plasticizer enhances the benefits of the collagen coating.

The coating solution is maintained at about room temperature when the suture is immersed therein for a period of time sufficient to provide a suitable coating, preferably from about 1 to about 20 minutes, and more preferably from about 5 to about 15 minutes. Preferably, the soaking time is sufficient to allow the suture to swell and the collagen solution to penetrate the interstices of the suture where it is later cross-linked.

The suture can be immersed in a coiled configuration or straight configuration. After immersion for the predetermined duration of time the suture is removed and secured to a frame.

The frame with the suture is then placed in a vacuum oven and heated to a temperature sufficient to effect the cross-linking of the collagen. When collagen is heated in the presence of water it becomes denatured, which is to be avoided in this process. Since the collagen is cross-linked above the denaturation temperature of from about 40° C. to about 60° C., water must be excluded. Hence, the suture is simultaneously vacuum dried at a pressure of less than about 1 torr and heated to a temperature of from about 70° C. to about 120° C. and more preferably from about 105° C. to about 115° C. The dehydrothermal cross-linking process is preferably maintained for about 10 to 20 hours, or until sufficient time has elapsed to effect a suitable degree of cross-linking. Cross-linking fixes the collagen and renders it insoluble in the tubing solution in which the suture will be stored. The suture is then allowed to cool down to room temperature before the vacuum is released.

After the suture is removed from the frame it is immersed in a tubing fluid for storage. Various compositions of tubing fluids are known in the art. A tubing fluid suitable for use in the method described herein includes water, isopropanol, and triethanolamine (TEA) in the following percentages: 12% water, 86.6% isopropanol, and 1.4% TEA.

Catgut sutures can be individually packaged and shipped in tubing fluid and stored for later use by a surgeon in an operation. When the catgut sutures are removed they retain the collagen coating and exhibit superior handling characteristics and fray resistance as opposed to sutures which have not been treated in accordance with the method described above. Examples of suture coating are provided below. Comparative Examples A and B are experimental controls which are not performed in accordance with the method described above. The remainder of the Examples illustrate the method described herein. Suture handling characteristics were tested manually by loosely tying an overhand knot in the suture and running the knot down the length of the suture. Surface roughness was estimated by tactile observation. Fraying was observed visually.

EXAMPLE 1

Collagen powder (SEEMED S, supplied by Kensey Nash Corporation, Exton Pa.) 0.06 grams was placed into a 100 cc glass beaker and 50 c.c of acidified pyrogen free water with a pH value of 3 was added to the collagen powder in the beaker. The mixture is stirred until the collagen was completely dissolved. The solution was allowed to settle and was stored in the freezer. Prior to use, the collagen coating solution was brought to room temperature. Coiled gut sutures were introduced into the collagen solution and were completely immersed for 2 minutes. The collagen coated gut samples were removed, uncoiled, and secured to a metal frame. The metal frame with coated sutures was then introduced into a vacuum oven and heated at 110° C. for 16 hours at a vacuum of less than a torr. After the heating cycle the oven was cooled to the room temperature, the vacuum released, and the metallic frame removed from the vacuum oven. At least 30 minutes was allowed to cool the frame and gut sutures. The sutures are removed from the frame and cut to the required length and stored in the gut tubing fluid containing 12.0 grams of water, 86.6 grams isopropanol and 1.4 grams triethanolamine.

Table top knot run down results showed that more than 15 knots could be put in. No fray was observed even after 12th knot run down.

EXAMPLE 2

Collagen powder (SEEMED S, supplied by Kensey Nash Corporation, Exton, Pa.) 0.06 grams was placed into a 100 cc glass beaker and 50 c.c of acidified pyrogen free water having a pH value of 3 was added to the collagen powder in the beaker. The mixture was stirred until the collagen was completely dissolved. To this collagen solution 0.004 grams of glycerol plasticizer was added. The mixture was stirred for an additional 10 minutes and the solution allowed to settle. The collagen coating solution was stored in the freezer. Prior to use, the collagen solution was brought to room temperature. Coiled gut sutures were introduced into the collagen solution and were completely immersed for 10 minutes. The coated collagen gut sutures were then removed, uncoiled, and secured to a metal frame. The metal frame with coated sutures was then introduced into a vacuum oven and heated at 110° C. for 16 hours at less than a torr. After the heating cycle the oven was cooled to room temperature, the vacuum released, and the metal frame removed from the vacuum oven. At least 30 minutes was allowed to cool the frame and gut sutures. Upon removal from the frame the sutures were cut to the required length and stored in the gut tubing fluid containing 12.0 grams of water, 86.6 grams isopropanol and 1.4 grams triethanolamine.

The collagen coated gut sutures exhibited smooth run down. Table top knot run down results showed that more than 15 knots could be put in. No fray was observed even after 15th knot run down.

Comparative Example A

Uncoated gut sutures were secured to a metal frame. The metal frame with uncoated gut sutures was heated in a vacuum oven at 110° C. for 16 hours at a pressure of less than a torr. The resulting gut sutures were then introduced into gut tubing containing 12.0 grams of water, 86.6 grams isopropanol and 1.4 grams triethanolamine. Upon testing for handling characteristics, the gut sutures frayed immediately.

Comparative Example B

A small amount of collagen gel (designated as SEEMED SA-1, and supplied by Kensey Nash Corporation of Exton, Pa.) was taken onto a paper and smoothly rubbed on the gut sutures throughout. The collagen gel-coated gut samples were secured to a metal frame, and the metallic frame with coated sutures was then introduced into a vacuum oven and heated at 110° C. for 16 hours at a vacuum of less than a torr. After the heating cycle the oven was cooled to room temperature, the vacuum released, and the metal frame removed from the vacuum oven. At least 30 minutes was allowed to cool the frame and gut sutures. The sutures were removed from the frame and cut to the required length and stored in gut fluid containing 12.0 grams of water, 86.6 grams isopropanol and 1.4 grams triethanolamine.

The coated sutures were tested for knot run down on a table top. The gel coating was observed to be not uniform on the suture. Run down was rough and the sutures frayed soon after 3 knot run downs.

As can be seen from the above Examples, uncoated gut sutures (Comparative Example A) had poor handling characteristics. Surprisingly, sutures coated with unacidified collagen gel (Comparative Example B) also had poor handling characteristics as compared to Examples 1 and 2, in which the collagen solution was prepared from a collagen powder dissolved in acidified water. Use of acidified water is an important feature of the method. In Example 2 glycerol was added to the coating solution as a plasticizer.

Referring now to FIG. 1, a suture-containing package 10 includes an envelope 11 sealed around the edges 12 with collagen coated gut suture 14 immersed in tubing fluid 13. The envelope is fabricated from a material impervious to fluid, such as plastic or metal foil. The suture and tubing fluid can be sterilized by heat treatment to a suitable sterilization temperature and/or by incorporating suitable germicides in the tubing fluid, such as e.g., phenyl mercuric benzoate. The suture 14 and tubing fluid 13 are as described above. In another embodiment 20 the container 21 is a tubular ampule and sealed with a stopper 12. The container can be fabricated from glass or plastic. The collagen coated gut suture 24 and tubing fluid 13 contained in the ampule 21 are as described above.

It will be understood that various modifications may be made to the embodiments described herein. The above description should not be construed as limiting but merely as exemplification of preferred embodiments. Those skilled in the art will envision other modifications within the scope and spirit of the claims appended hereto.

What is claimed is:

1. A gut suture having a dehydrothermal cross-linked collagen coating which is substantially insoluble in a tubing solution containing water and an alcohol.

2. The gut suture of claim 1 wherein said coating further includes a plasticizer.

3. The gut suture of claim 2 wherein the plasticizer is glycerine.

\* \* \* \* \*